_United States Patent_ [19]

Chance et al.

[11] 3,963,351
[45] June 15, 1976

[54] MULTI-CHANNEL OPTICAL TIME-SHARING APPARATUS HAVING A ROTATING FILTER WHEEL WITH POSITION-ENCODING MEANS

[76] Inventors: Britton Chance; Victor Legallais; John R. Sorge; Norman C. Graham, Jr., all of Philadelphia, Pa.

[22] Filed: Apr. 14, 1975

[21] Appl. No.: 567,946

[52] U.S. Cl. ................................. 356/85; 250/227; 250/231 SE; 250/458; 250/461 B; 356/188
[51] Int. Cl.² ........................ G01J 3/30; G01J 3/48
[58] Field of Search ........................ 356/73, 85, 188; 250/226, 227, 231 SE, 233, 458, 461, 461 B

[56] References Cited
UNITED STATES PATENTS

| | | | |
|---|---|---|---|
| 3,374,477 | 3/1968 | Ejiri et al. | 250/231 SE |
| 3,811,777 | 5/1974 | Chance | 356/73 |
| 3,828,173 | 8/1974 | Knepler | 356/188 |

_Primary Examiner_—Vincent P. McGraw
_Attorney, Agent, or Firm_—Herman L. Gordon

[57] ABSTRACT

A multi-wavelength time-sharing apparatus usable in various different configurations of optical measuring equipment to provide a plurality of time-shared optical channels and including appropriate circuitry. The apparatus employs a turbine-driven filter wheel having a shaft position-encoding arrangement consisting of a hollow shaft portion which is internally illuminated. The hollow shaft portion has two sets of spaced apertures cyclically communicating with respective angularly spaced pairs of externally fixedly mounted phototransistors which are sequentially illuminated as the shaft portion rotates and which produce timing pulses which drive Schmitt triggers, which, in a typical embodiment, in turn produce pulses compatible with a logic circuit employed to decode the phototransistor signals into triggers for driving a 4-channel switched gain equalizer, a dark current clamp, and detector gates. Appropriate selection of the signals enables the instrument to function as a fluorometer or a spectrophotometer.

17 Claims, 7 Drawing Figures

MULTI-CHANNEL OPTICAL TIME-SHARING APPARATUS HAVING A ROTATING FILTER WHEEL WITH POSITION-ENCODING MEANS

This invention relates to time-sharing optical apparatus, and more particularly to multi-wavelength optical measuring apparatus of the type employing a rotating filter disc or similar multi-wavelength rotating filter element.

A main object of the invention is to provide a novel and improved time-sharing apparatus for use in multi-channel and similar optical measuring instruments, which affords flexibility and versatility in optical measurements, and which offers the advantages of high speed of time-sharing, simplicity and compactness, and which causes minimal acoustic and electrical disturbance to the associated experimental system.

A further object of the invention is to provide an improved optical time-sharing instrumentation system suitable for use in various instrumental configurations, such as in a fluorometer, a reflectometer, a multi-channel spectrophotometer, or the like, the improved system being simple in construction, being reliable in operation, being quiet in operation, being compact in size, and employing relatively inexpensive components.

A still further object of the invention is to provide an improved turbine-driven multi-wavelength time-sharing optical filter disc apparatus which may be utilized in a wide range of different optical configurations, such as in a spectrofluorometer, a reflectometer, or a spectrophotometer with four wavelength channels, the apparatus including reliable and accurate shaft position-encoding means and associated circuitry having gate-generating means reliably controlled by said encoding means and operting to decode shaft-position signals so as to coordinate the wavelength detection and output signal circuitry in a positive and dependable manner with the shaft positions and to insure the proper phasing of the rotating filter disc with the associated gate portions of the apparatus at all times, the apparatus being usable in a variety of fluorometer, reflectometer, and spectrophotometric combinations of important significance in a wide range of experiments, such as in experiments with intact tissues, perfused organs, suspensions of cells and subcellular organelles, and the like.

Further objects and advantages of the invention will become apparent from the following description and claims, and from the accompanying drawings, wherein FIG. 1 is a longitudinal vertical cross-sectional view taken through a typical rotating-disc position-encoding apparatus constructed in accordance with the present invention.

Figure 4:
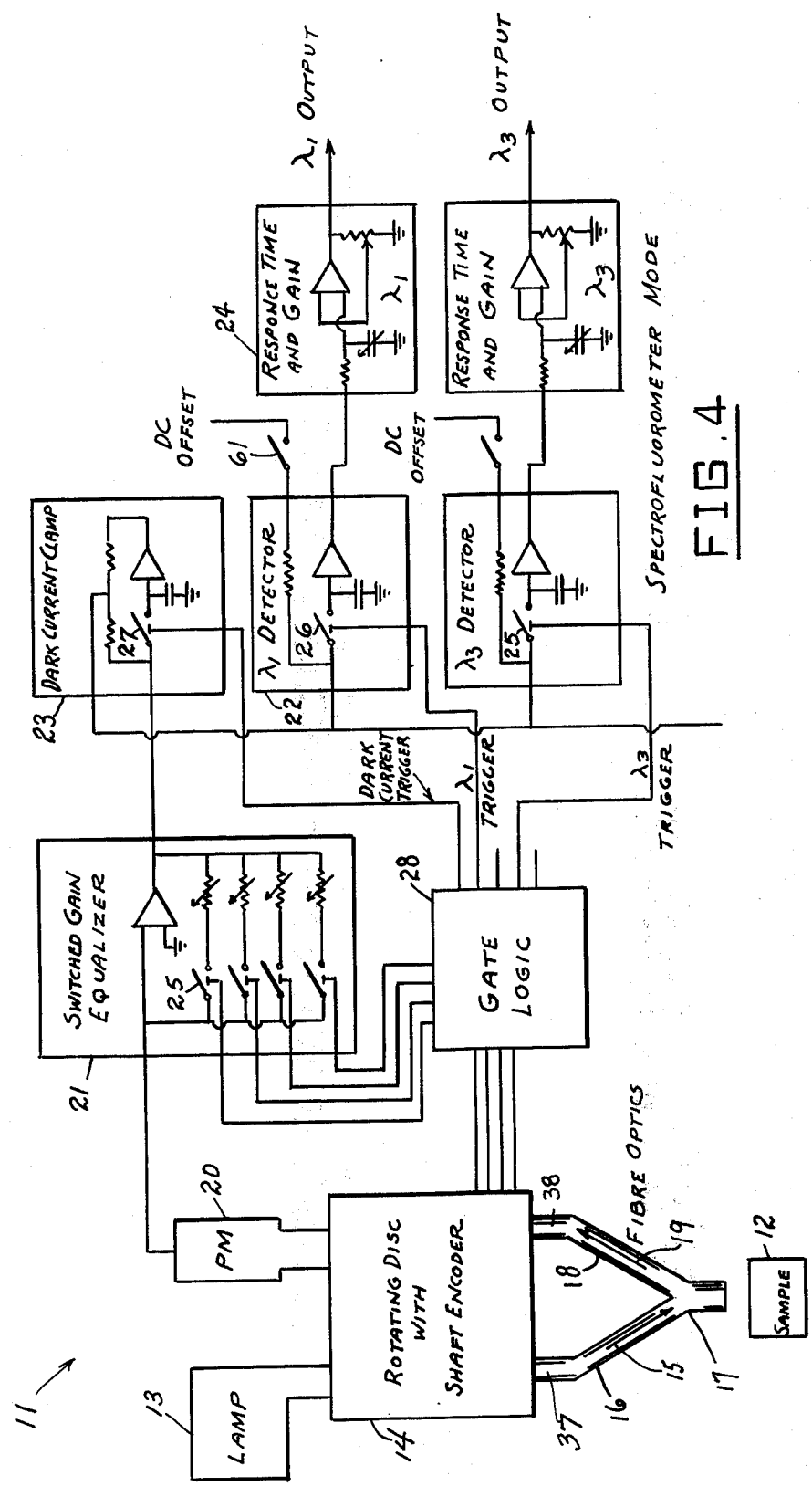
FIG. 4 is a schematic block diagram of a typical spectrofluorometer according to the present invention employing the rotating filter disc and shaft position-encoding structure of FIGS. 1, 2 and 3.

Referring to the drawings, and particularly to FIG. 4, 11 generally designates a typical multi-wavelength photometer employing time-sharing apparatus according to the present invention, arranged as a spectrofluorometer to measure the fluorescence responses of a sample 12 undergoing test.

Figure 6:
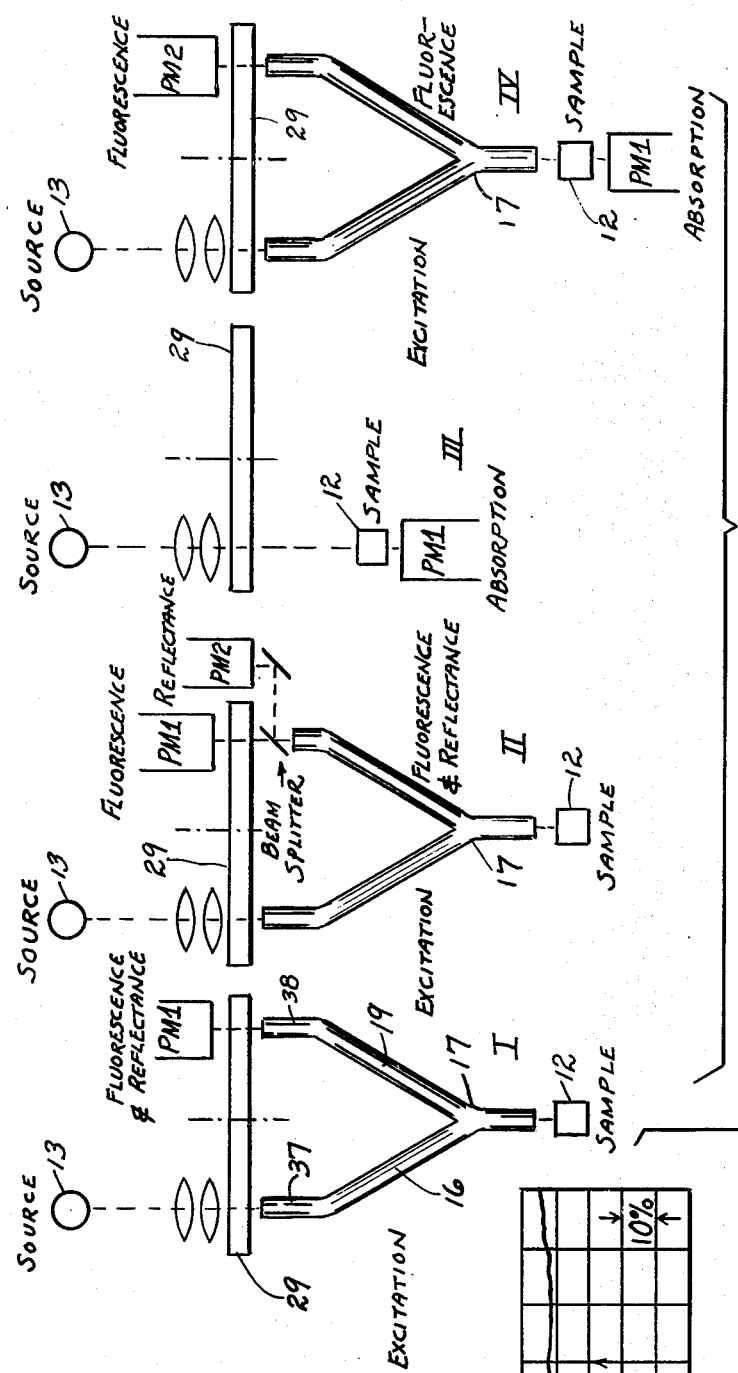
FIG. 6 is a schematic diagram showing four possible instrument configurations employing the time-sharing apparatus of the present invention.

For example, the spectrofluorometer 11 may be employed for the time-sharing measurement of PN (pyridine nucleotide) and Fp (flavoprotein) fluorescence in the Configuration I arrangement diagrammatically illustrated in FIG. 6.

In the typical arrangement illustrated in FIG. 4 for examining PN and Fp fluorescence of a sample 12, light from a source 13 is processed by a rotating filter disc and encoding assembly 14 to generate cyclically a first excitation beam 15 of suitable excitation wavelength, such as 366 nm, which is directed through one arm 16 of a Y-shaped light pipe assembly 17 to the sample undergoing treatment in the cuvette 12, and the resultant cyclical fluorescence emission wavelength of interest, in this case 450 nm, is simultaneously directed back through the other arm 18 of the light pipe assembly as an emission beam 19 through the rotating filter disc and encoding assembly 14 to photomultiplier tube 20, to thereby generate cyclical pulse signals representing the PN fluorescent response.

At the next phase in the operaton of the device 14, as will be presently explained, a second excitation wavelength, such as 460 nm, forms the excitation beam 15, (for exciting the Fp in the sample), and simultaneously the resultant fluorescence of interest, of wavelength 520 nm for Fp, forms the emission beam 19, which is conveyed through the assembly 14 to the photomultiplier tube 20 to thereby generate cyclical pulse signals representing the Fp fluorescent response.

The time-shared photomultiplier signals are passed through a switched gain equalizer 21, employed for suitably equalizing the signals at the beginning of a test, adjusted against a suitable d.c. offset signal by means of a switch 61, to thereafter provide compensation of the photomultiplier signals, and the compensated time-shared signals are delivered to respective time-shared sample-and-hold detector channels 22, with dark current corrections provided by a dark current clamp circuit 23, in a manner to be presently described. The respective time-shared, compensated, dark current-corrected signals are then delivered to respective amplifier circuits 24 whose outputs represent the fluorescence reponses of the compounds of interest in the sample under test, in this case, the PN and Fp as above mentioned.

In the above-described two-channel time-shared system, the necessary synchronization of the switched gain equalizer circuits 21 with the detector channels 22 and the application of dark current corrections to the resultant pulse signals are provided by respective electronic switches 25, 26 and 27 controlled by a gate logic circuit 28 which is driven by the rotating disc and shaft encoder assembly 14, now to be described.

Figure 1:
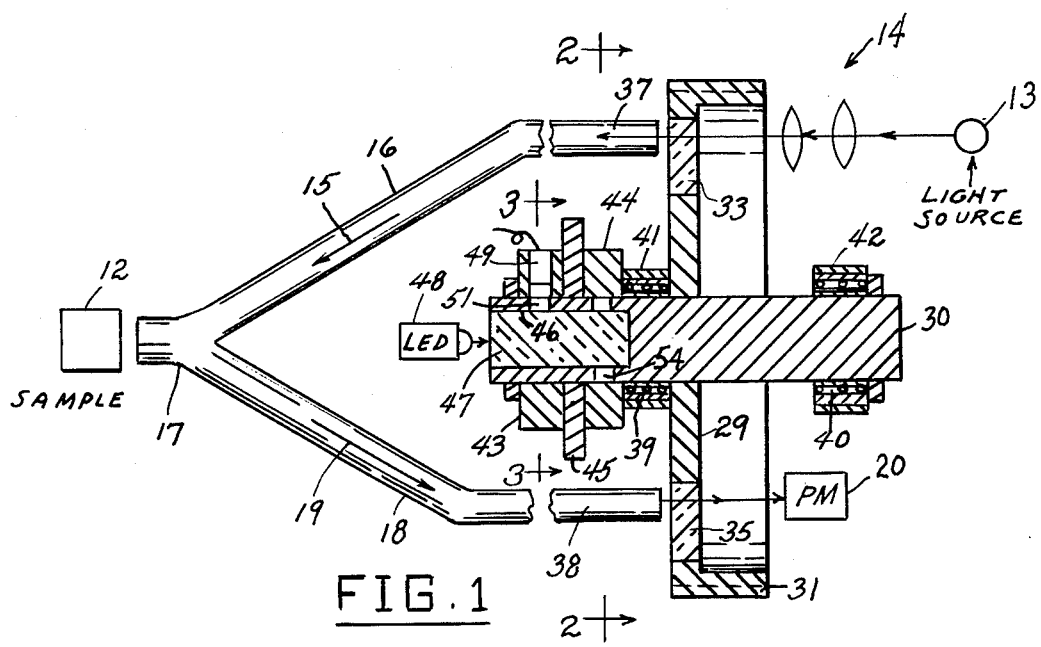
Figure 2:
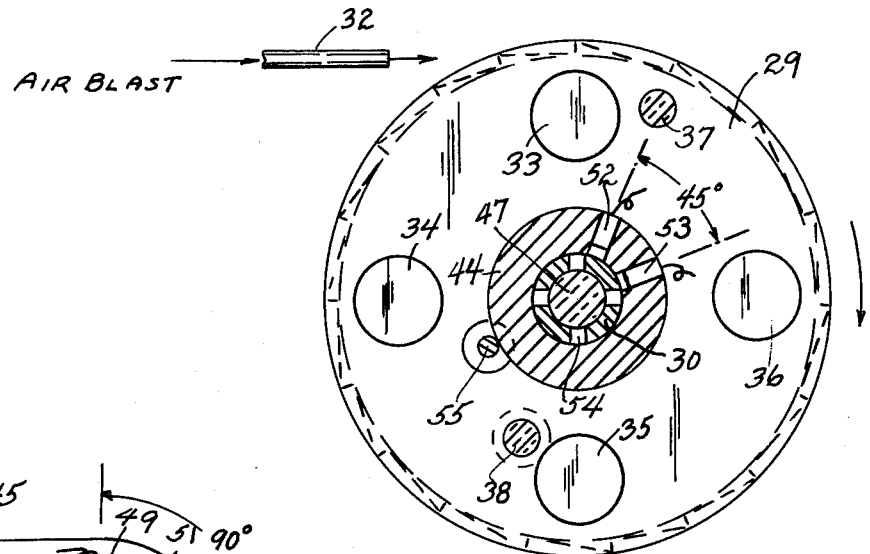
FIG. 2 is a transverse cross-sectional view taken substantially on the line 2—2 of FIG. 1.
Figure 3:
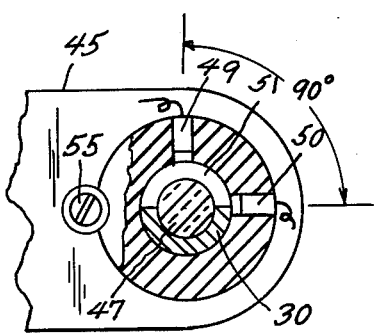
FIG. 3 is a transverse cross-sectional view taken substantially on line 3—3 of FIG. 1.

Referring now to FIGS. 1, 2 and 3, the device 14 comprises a disc member 29 mounted on a rotatable shaft 30, the disc member having a suitably serrated peripheral drum portion 31 which is driven by an air blast from an air supply conduit 32, as shown in FIG. 2. The disc 29 is provided with four equally spaced filters 33 to 36 at equal radial distances from the disc axis, designed to pass the respective required wavelengths. The light source 13 is suitably mounted in alignment with the end portion 37 of light pipe arm 16, as shown. The photomultiplier tube 20 is oppositely mounted, similarly in alignment with the end portion 38 of light pipe arm 19 at a different radial distance from shaft 19 such that phosphorescence induced in an emission filter by light source 13 is not in the same area of the filter as that seen by photomultiplier tube 20.

Shaft 30 is rotatably mounted in ball bearing assemblies 39 and 40 carried by stationary supports 41 and 42 on opposite sides of disc 29. Shaft 30 extends rotatably through respective ring members 43 and 44 which are adjustably secured to opposite sides of a fixed bracket member 45 through which shaft 30 rotatably extends, as shown in FIG. 1. The shaft 30 extends leftwardly beyond ball bearing assembly 39, and this leftwardly extending shaft end portion is formed with a cylindrical cavity 46 in which is secured a body of light-transmitting and diffusing material 47, such as Plexiglas, or an equivalent type of material, serving as a light pipe and diffuser, which fills the cavity. The exposed end of body 47 is illuminated by a GaAs light-emitting diode 48 fixedly mounted in a suitable manner adjacent said exposed end of body 47.

Radially mounted in ring 43 so as to be illuminated by body 47 are two phototransistors 49 and 50 spaced 90° around the axis of shaft 30 and being coplanar with a 180°-extending peripheral slot 51 formed in the wall of cavity 46. Radially mounted in a similar manner in ring 44 are two phototransistors 52 and 53 spaced 45° apart around the shaft axis and being respectively sequentially registrable with four 90° spaced apertures 54 formed in the wall of cavity 46. The rings 43, 44 may be adjusted angularly relative to each other and may be clamped in adjusted positions by any suitable means, for example, by headed clamping screws 55 threadedly engaged with bracket 45. With the rings held stationary, as the encoder shaft 30 rotates inside them, the phototransistors are illuminated sequentially. The two rightward transistors 52, 53 are illuminated through the four small apertures 54 and produce pulses 86, 87 every 90° of rotation, with a relative phase of 45° (see FIG. 5). The pair of phototransistors 49, 50 in the leftward ring 43 are illuminated for 180° and are then dark for 180°, producing square waves 58, 59 with a relative phase of 90°. The axial rings 43, 44 are independently adjustable, allowing them to be phased properly with respect to the rotating disc 29.

Figure 5:
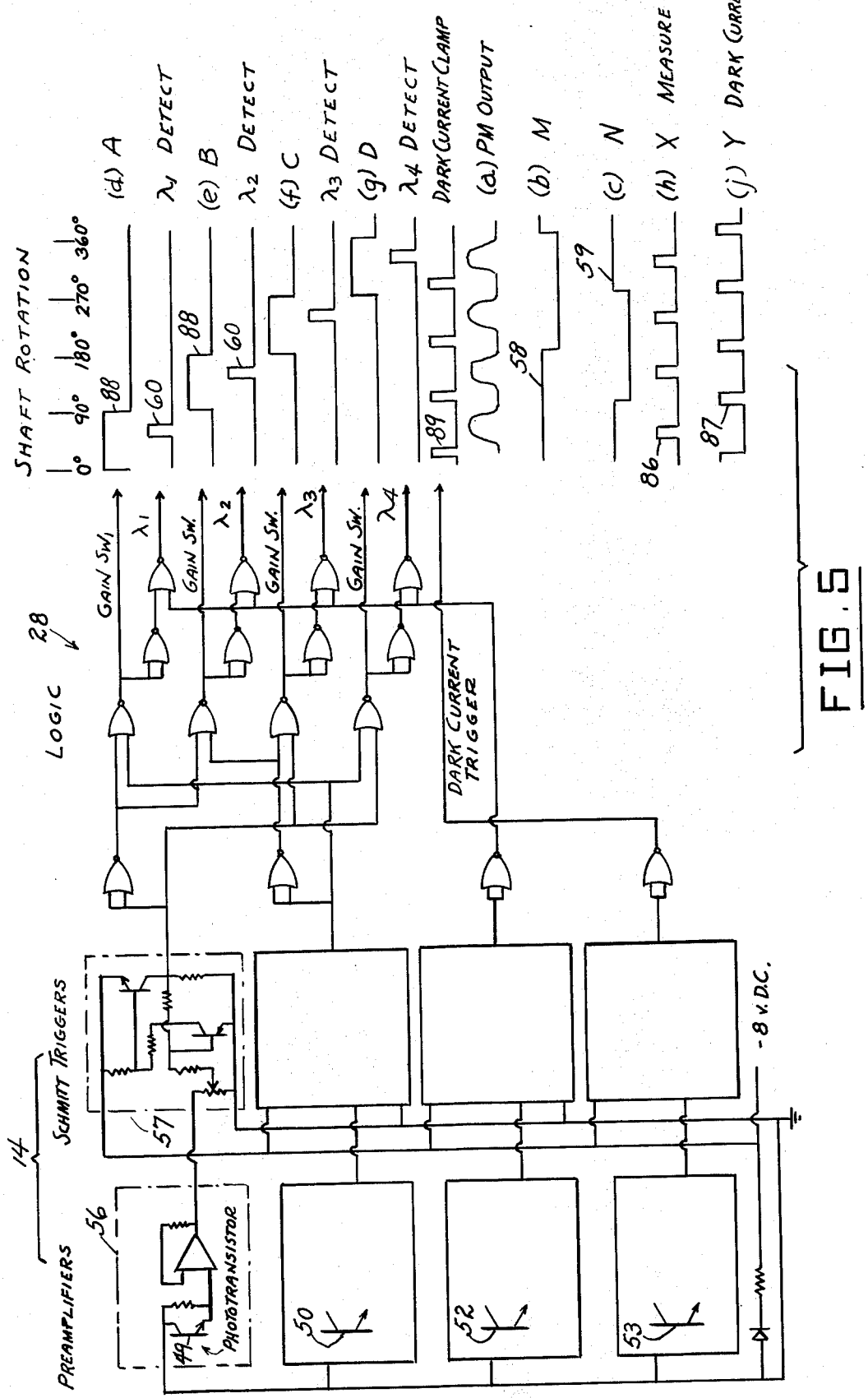
FIG. 5 is a schematic diagram of the preamplifier, Schmitt trigger and logic circuitry which may form part of an optical time-sharing system of the present invention.

As shown in FIG. 5, a four-channel amplifier (such as National Semiconductor Model LM 3900) serves as a preamplifier and line-driver for the phototransistors 49, 50, 52, 53, and is small enough to be mounted in the enclosure containing the rotating disc assembly. The amplifiers 56 drive Schmitt triggers 57, producing pulses compatible with the logic circuit 28 employed to decode the phototransistor signals into triggers 88 for driving the four-channel switched gain equalizer 21, triggers 89 for driving the dark current clamp 23, and triggers 60 for driving the detector gates 22 shown in FIG. 4. The analog switch elements 25 of gain equalizer 21 may be similar to RCA type CD 4016AE, while the rest of the circuitry may use 2N4221 type J-FET switches. In FIG. 5, 58, 59 are the outputs of the two quadrature phototransistors 49, 50 (after being squared-up by the Schmitt triggers), and 86 is the squared-up output of the phototransistor 52 before being decoded into pulses 60. The decoded pulses consist of four equalization gate pulses 88, four detector gate pulses 60, and the dark current clamp gate pulses 89. Appropriate selection of these signals enables the rotating filter disc and associated shaft encoding and decoding assembly to be employed in a wide range of instrument configurations, including the above-described fluorometer configuration (Configuration I of FIG. 6), a multi-channel spectrophotometer configuration (Configuration III of FIG. 6) or various other configurations such as those shown in Configurations II and IV of FIG. 6. The dark current clamp pulses 89 are not employed in the spectrophotometer mode. Note that Configurations I and II may be employed for both fluorometer and reflectometer tests. DC bucking may be provided (DC offset) for the fluorometer configuration, as shown in FIG. 4, or for single-ended detector configurations, while dual wavelength spectrophotometer configurations would employ the circuitry of 23 as the detector for the reference wavelength, being driven by a detect pulse 60 instead of the dark current clamp pulse 89. Here the dark current clamp is in essence subtracting the reference signal instead of the dark current signal.

As above described, FIG. 4 illustrates use of the apparatus in a dual channel fluorometer of Configuration I. Only $\lambda 1$ and $\lambda 3$ are detected in this case; $\lambda 2$ and $\lambda 4$ are the excitation wavelengths and therefore the switch and detector pulses for $\lambda 2$ and $\lambda 4$ are not used.

Figure 7:
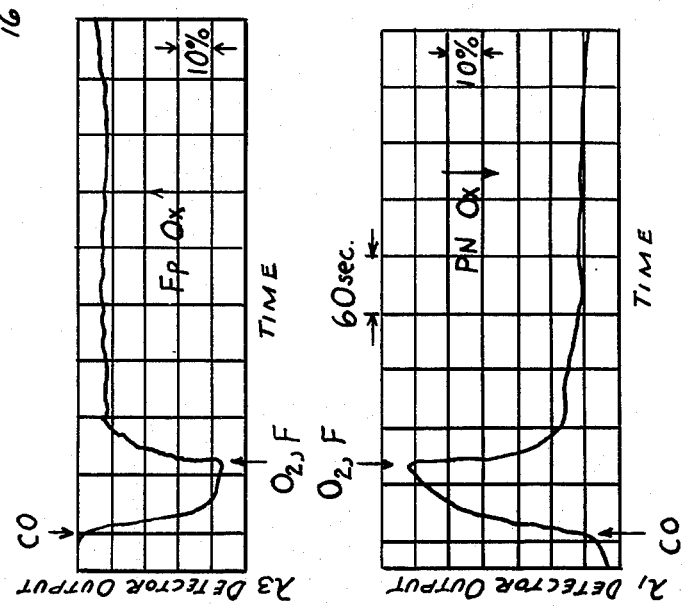
FIG. 7 shows typical graphs obtained by the use of a spectrofluorometer configuration according to the present invention in measuring the time course of fluorescence changes in a perfused heart.

The simultaneous measurement of the fluorescence of reduced PN and oxidized Fp, as previously described, by means of the apparatus of Configuration I with the above-described filter combination (366 nm for excitation of PN, 450 nm for emission thereof, and 460 nm for excitation of Fp and 520 nm for emission thereof) provides a versatile and useful approach to the study of the oxidation-reduction states of perfused organs, and intensive work has been carried out with perfused liver and heart. Other possibilities are kidney, brain, and specialized organs, such as the carotid body, adrenal cortex, etc. FIG. 7 illustrates the response of Fp (top trace) and PN (bottom trace) components of perfused heart measured by surface fluorescence, employing Configuation I. An exchange of oxygen-saturated perfusate to carbon monoxide-saturated perfusate at the point marked "CO" causes a decrease of the fluorescence of Fp and an increase of that of PN, since it is the oxidized and reduced forms, respectively, of these components that are fluorescent. Using the fluorescence of the organ in the presence of oxygen as the baseline, the decrease of Fp fluorescence caused by the transition from oxygen to carbon monoxide was 42 percent while the increase of PN fluorescence reached about 60percent when CO infusion was terminated. These large percentage changes of fluorescence indicate that other fixed fluorescence signals, such as the phosphorescence of the emission filters or scattering or leakage of excitation light through the secondary filter are small. Furthermore, since timesharing of the two signals is employed, there is no possibility of cross-reactions at the four wavelengths.

Since the organ is saturated with carbon monoxide which is tightly bound to cytochrome oxidase, reperfusion with oxygensaturated medium ("$O_2$") causes only a small response of Fp or PN. However, a flash ("F") from a liquid dye laser at 585 nm releases the carbon monoxide from the oxidase and allows it to react with oxygen. (See U.S. Pat. No. 3,830,222 to Britton Chance, issued Aug. 20, 1974). Thus, the arrow indicating the flash (F) inititates the sequence of events which follow: the cytochrome oxidase : CO molecules to which oxygen has diffused by the time of the flash are photolyzed and the cytochrome oxidase reacts rapidly with oxygen, leading to electron transport through the respiratory chain to oxidize reduced Fp and PN, marked by abrupt shifts of the traces in the first second. The further slow changes of the traces indicates the further diffusion of oxygen to the total tissue volume between the capillary vessels of the heart. The high signal-to-noise ratio of the apparatus of the present invention allows measurement of the reaction kinetics with a half-time of 50 msec on an oscillograph.

The following is a table giving some examples of the application of the different configurations of FIG. 6, employing time-sharing apparatus of the present invention, for optically testing various components:

$$A = M \cdot N \; ; \; C = \overline{M} \cdot \overline{N}$$

$$B = M \cdot \overline{N} \; ; \; D = \overline{M} \cdot N$$

The resulting signals (derived from logic circuit 28) are shown at lines (d), (e), (f) and (g), respectively labelled "A", "B", "C" and "D". It will be seen that the true (or high) level of A is uniquely identified with $\lambda 1$ and the dark interval immediately preceeding $\lambda 1$, B is identified with $\lambda 2$, etc.

These four signals then can be used to process the information from the two 45°-offset phototransistors 52, 53 in the rightward mounting ring 44, shown in lines (h) and (j), labelled "X" and "y". Signals X and y only indicate the presence of a measure interval and a dark interval but are related via signals A through D to their respective wavelengths. For instance, the Boolean expression to decode the measure interval for $\lambda 3$ is $\lambda 3m = C \cdot X$, while its associated dark interval is $\lambda 3d = C \cdot Y$.

The four signals A through D are also used directly to actuate the switches 25 in the feedback circuitry of the input stage 21 to implement the switchable gain func- Table 1

| Application | Channels | Component | Fluorescence nm | | Absorption or (R) Reflectance nm | | | |
|---|---|---|---|---|---|---|---|---|
| | | | $\lambda_{ex}$ | $\lambda_{em}$ | $\lambda_1$ | $\lambda_2$ | $\lambda_3$ | $\lambda_4$ |
| 1. Fluorometer (I) | 2 | PN | 366 | 450 | — | — | — | — |
| | | Fp | 460 | 520 | — | — | — | — |
| 2. Fluorometer/ (II) Reflectometer | 2 | PN | 366 | 450 | (R)366 | 366 | — | — |
| 3. Fluorometer (I) | 2 | Merocyanine | 577 | 640 | — | — | — | — |
| 4. Fluorometer/ Spectrophoto-meter (IV) | 2 | Merocyanine | 577 | 640 | 620 | 630 | — | — |
| 5. Fluorometer/ Spectrophoto-meter (IV) | 2 | PN | 366 | 450 | — | — | — | — |
| | 2 | Cytochrome c | — | — | 550 | 540 | — | — |
| 6. Spectrophoto-meter (III) | 2 | Cytochrome c Catalase-$H_2O_2$ | — | — | 550 | 540 | — 640 | — 660 |
| 7. Spectrophoto-meter (III) | 2 | Cytochrome c Copper | — | — | 550 | 540 | — 830 | — 940 |
| 8. Spectrophoto-meter (III) | 2 | Cytochrome a +a3 Phenol Red | — | — | 445 — | 460 — | — 540 | — 560 |
| 9. Spectrophoto-meter (III) | 3 | Cytochrome c1 Cytochrome b$\gamma$ Cytochrome b$\chi$ | — | — | 554 — — | — 566 — | — — 560 | 540 540 540 |
| 10. Spectrophoto-meter (III) | 4 | Cytochrome a +a3 Copper Oxymyoglobin Oxymyoglobin | — | — | 605 — 587 — | 620 — 581 — | — 830 — 700 | — 940 — 800 |

With reference to FIG. 5, the operation of the gate logic circuit 28 will be understood from the following discussion:

Light from the excitation light source 13 is chopped by the rotating disc 29 into four different wavelengths by the filters 33 to 36 mounted in the disc (assuming spectrophotometric and not fluorometric operation) and appears as in line (a). The shaft encoder assembly must provide information which enables measurements made with this light to be decoded. Specifically, shaft position must be known at any instant of time, so that time can be related to the four wavelengths.

The output of the two leftward phototransistors 49, 50 (FIGS. 1, 2 and 3) as seen at the output of their associated Schmitt trigger circuits 57 appear as shown in lines (b) and (c). These two signals will be seen to be quadrature square waves 58, 59 with a frequency equal to the rotational frequency of the disc 29. If these signals are labelled M and N, the following Boolean functions can be implemented with digital logic:

tion allowing the calibration of all four wavelengths to an arbitrary constant.

The electrical circuitry thus decodes (using positive true COS/MOS NOR gates) the quadrature square waves 58, 59, the dark interval pulses 87 and the measure interval pulses 86 to provide the gating signals for the detection and dark current clamping for the four different wavelengths as well as the control of the swithable gain signal equalizer 21.

The gain equalizer circuits 21 are of a type described in B. Chance, N. Graham, J. Sorge and V. Legallis, Rev. Sci. Instr., 43, 62 (1972). The dark current clamp circuit 23 and detector circuits 22 are basically sample-and-hold circuits similar to those described in "Waveforms", B. Chance, V. W. Hughes, E.F. MacNichol, Jr., D. Sayre, and F.C. Williams, Eds., MIT Radiation Laboratory Series, Boston Technical Publishers, Lexington, Mass., 1964, p. 501. The detectors 22 are provided with control switch means 61 for applying a bucking DC voltage in the fluorometer (Configuration 1) arrangement which may be switched off for the dual wavelength spectrophotometer configuration.

Use of the apparatus as a "double" dual wavelength spectrophotometer (Configuration III) of course requires one more "dark current clamp" circuit, but it will be readily understood that the apparatus may be easily adapted from one configuration to another.

In the dual wavelength mode the dark current clamp circuit is not used as such, but because it is driven by a detect interval pulse 60 it functions as a reference wavelength detector. Thus there is a need for an additional one of such a circuit in the "double" dual wavelength configuration.

The wavelength forms shown in FIG. 5 apply to any mode of operation, the only changes required being to route the appropriate pulses to the correct sample/hold detector circuits.

While a specific embodiment of an improved multi-channel time-sharing apparatus for optical instruments has been disclosed in the foregoing description, it will be understood that various modifications within the spirit of the invention may occur to those skilled in the art. Therefore it is intended that no limitations be placed on the invention except as defined by the scope of the appended claims.

What is claimed is:

1. In a multi-wavelength optical instrument of the type including a plurality of optical channels provided with respective gain equalizer means and signal detection means, a rotating filter member having a plurality of wavelength filters spaced around its axis to define said optical channels and provided with a supporting shaft having a hollow portion, means to illuminate said hollow shaft portion internally, respective signal-generating photosensitive means associated with the gain equalizer means and the signal detection means mounted externally adjacent said hollow shaft portion, said hollow shaft portion having means formed to illuminate said respective photosensitive means so as to generate respective cyclic sets of long and short pulses, and means to decode said pulses to derive respective cyclic gating pulses for said gain equalizer means and signal detection means.

2. The multi-wave optical instrument of claim 1, and wherein said instrument includes dark current clamp means and said decoding means includes means to derive cyclic gating pulses for said dark current clamp means from said first-named sets of pulses.

3. The multi-wave optical instrument of claim 1, and wherein the means to illuminate said hollow shaft portion internally comprises a body of transparent light-diffusing material substantially filling said hollow shaft portion and having an exposed surface, and a light source mounted adjacent said exposed surface.

4. In a multi-wave optical instrument of the type including a plurality of optical channels provided with respective gain equalizer means and respective measure signal detection means, a rotating filter member having a plurality of wavelength filters spaced around its axis to define said optical channels and provided with a supporting shaft having a hollow portion, means to illuminate said hollow shaft portion internally, first signal-generating photosensitive means mounted adjacent said hollow shaft portion, said hollow shaft portion having means formed to illuminate said first photosensitive means so as to generate cyclically relatively long pulses, second signal-generating photosensitive means mounted adjacent said hollow shaft portion, said hollow shaft portion having means formed to illuminate said second photosensitive means so as to generate cyclic sets of short pulses, and means to decode said long pulses and short pulses respectively to derive cyclic gating pulses for said gain equalizer means and cyclic gating pulses for said measure signal detection means.

5. The multi-wave optical instrument of claim 4, and wherein the first photosensitive means comprises a pair of angularly spaced phototransistors and the hollow shaft portion has a relatively long peripherally extending aperture arranged sequentially to illuminate said spaced phototransistors.

6. The multi-wave optical instrument of claim 5, and wherein said second signal-generating photosensitive means comprises a phototransistor and said hollow shaft portion is formed with spaced apertures corresponding in number to the number of filters and arranged sequentially to illuminate said last-named phototransistor.

7. The multi-wave optical instrument of claim 4, and wherein said instrument includes dark current clamp means and said decoding means includes means to derive cyclic gating pulses for said dark current clamp means from said short pulses.

8. The multi-wave optical instrument of claim 7, and wherein said second photosensitive means comprises a pair of angularly spaced phototransistors, said hollow shaft portion being formed with spaced apertures corresponding in number to the number of effective filters and arranged sequentially to illuminate said spaced phototransistors to derive cyclic pairs of short pulses, said decoding means including means to derive respective time-spaced cyclic gating pulses for the measure signal detection means as well as for the dark current clamp means from said cyclic sets of short pulses.

9. The multi-wave optical instrument of claim 4, and wherein said instrument includes dark current clamp means and wherein the first photosensitive means comprises a first pair of angularly spaced phototransistors and the hollow shaft portion has a relatively long peripherally extending aperture arranged sequentially to illuminate said spaced phototransistors, whereby to generate said relatively long pulses, and wherein said second photosensitive means comprises a second pair of angularly spaced phototransistors, said hollow shaft portion being formed with spaced apertures corresponding in number to the number of effective filters and arranged sequentially to illuminate said second pair of phototransistors, whereby to generate said cyclic sets of short pulses, said decoding means including means to derive respective time-spaced gating pulses for the gain equalizer means from the long pulses and means to derive respective time-spaced cyclic gating pulses for the measure signal detection means and for the dark current clamp means from the cyclic sets of short pulses.

10. The multi-wave optical instrument of claim 9, and wherein said relatively long peripherally extending aperture comprises a slot of approximately 180° in angular extent formed in the wall of said hollow shaft portion.

11. The multi-wave optical instrument of claim 9, and wherein said first pair of phototransistors are spaced apart by approximately 90°.

12. The multi-wave optical instrument of claim 9, and wherein said second pair of phototransistors are spaced apart by approximately 45°.

13. The multi-wave optical instrument of claim 9, and wherein the instrument includes a substantially Y-shaped light pipe having light beam-transmitting legs with ends located to register simultaneously with a pair of spaced filters carried by said rotating filter member.

14. The multi-wave optical instrument of claim 4, and wherein the instrument is provided with respective supporting ring members surrounding said hollow shaft portion, means for adjustably securing said ring members in fixed positions, and means for mounting said first and second photosensitive means in said ring members in positions to be cyclically illuminated by said hollow shaft portion.

15. The multi-wave optical instrument of claim 4, and wherein the means to illuminate said hollow shaft portion internally comprises a body of transparent light-diffusing material substantially filling said hollow shaft portion and having an exposed end, and a light source mounted adjacent said exposed end, the wall of the hollow shaft portion having an approximately 180° peripheral slot adjacent the first photosensitive means, and the wall of said hollow shaft portion having a plurality of evenly angularly spaced apertures corresponding in number to that of the filters adjacent the second photosensitive means.

16. The multi-wave optical instrument of claim 15, and wherein the first photosensitive means comprises a first pair of phototransistors spaced apart by approximately 90° and the second photosensitive means comprises a second pair of phototransistors spaced apart by approximately 45°.

17. In a spectrofluorometer, a rotating filter member having a plurality of wavelength filters spaced around its axis, and respective excitation and fluorescent emission detection light path-defining means arranged to simultaneously transmit excitation light through one wavelength filter and fluorescence emission light through another wavelength filter, said light pathdefining means being at radial distances from the axis of rotation of said rotating filter member sufficiently different to prevent phosphorescence induced in said one filter from appearing in the fluorescence light path-defining means.

* * * * *